(12) United States Patent
Goldenberg

(10) Patent No.: US 8,163,685 B2
(45) Date of Patent: Apr. 24, 2012

(54) SOY SKIN CARE

(76) Inventor: Michael Goldenberg, Brooklyn, NY (US)

(*) Notice: Subject to any disclaimer, the term of this patent is extended or adjusted under 35 U.S.C. 154(b) by 182 days.

(21) Appl. No.: 12/419,397

(22) Filed: Apr. 7, 2009

(65) Prior Publication Data

US 2010/0256032 A1    Oct. 7, 2010

(51) Int. Cl.
*A61K 7/50* (2006.01)

(52) U.S. Cl. ........ 510/130; 510/136; 510/138; 510/141; 424/70.1

(58) Field of Classification Search .................. None
See application file for complete search history.

(56) References Cited

U.S. PATENT DOCUMENTS

| | | | |
|---|---|---|---|
| 2,876,164 A | 3/1959 | Ershaw et al. | |
| 5,871,743 A | 2/1999 | Chajuss | |
| 7,309,688 B2 * | 12/2007 | Seiberg et al. | 514/19.3 |
| 2005/0025725 A1 | 2/2005 | Schultz et al. | |
| 2006/0251750 A1 | 11/2006 | Tabor | |

* cited by examiner

*Primary Examiner* — Necholus Ogden, Jr.
(74) *Attorney, Agent, or Firm* — Yitzy Nissenbaum; Israel Nissenbaum

(57) ABSTRACT

Skin care preparation materials comprising substantial amounts of food grade soy flour in soap bars in separate soap bars suitable for detoxification and makeup removal, exfoliation and moisturization. The food grade soy flours are of differing types and fat content as well as particle size and lecithin content suitable for each of the skin care purposes. A seriatim regimen of skin care with the soap bars is used for maximum skin care effect.

16 Claims, No Drawings

SOY SKIN CARE

FIELD OF THE INVENTION

This invention relates to skin care preparations and regimens and particularly to skin care preparations having soy content, for detoxification, makeup removal, exfoliation, and moisturization, in addition to general cleansing.

BACKGROUND OF THE INVENTION

The field of skin care is rife with a plethora of skin care preparations and treatment devices. In addition to preparations for the treatment of skin conditions and maladies such as acne and eczema and conditions such as hives and rashes, all of which have their own treatments, there are a multitude of preparations for normal skin cleansing and maintenance regimens to stave off the ravages of aging and wrinkles. Skin cleansers encompass numerous soaps and crèmes such as the ubiquitous bar soaps, and the increasingly popular liquid soaps with different creams (creams and crèmes are used interchangeably herein), lotions and shampoos targeted and formulated for different body parts.

Specialty cleansers include makeup removal crèmes some of which have properties of detoxification with the removal of skin toxins. Soap bars, however, even with moisturizing material contents are not used for anything other than cleansing since they are universally known as detrimental dryers of skin and they are not of sufficient strength to detoxify or remove makeup. Bar cleansers are accordingly limited to general cleaning whereas creams and lotions are used for skin care such as makeup removal and exfoliation and for skin moisturization. Typical fatty acid soap bars are not classified as cosmetics and are not under FDA regulation.

Skin cells have a finite lifetime with dead skin cells tending to clog up pores, often resulting in an unhealthy skin appearance. The use of dead skin removal preparations or exfoliants are commonly part of skin care regimens, to bring fresh and healthy appearing skin to the surface. Skin moisturizing preparations prevent or retard the advent of wrinkles and cracked skin resulting from aging and harsh environmental conditions and are another essential part of the daily skin care procedures followed by many people and particularly women.

Existing skin care procedures entail the expenditure of large amounts of time, money and effort as well as requiring a multitude of materials and preparations to the point of extensive rituals. Furthermore, despite all the efforts, results are often deficient.

Soy derived materials have been touted as being beneficial and have been utilized in skin care preparations but only after they have been extensively processed into a cosmetic grade after having been refined, bleached and deodorized. Cosmetic grade soy is effectively of a concentrated form with harsh characteristics if extensively used and cannot be used in skin care preparations in quantities which exceed a fraction of one percent by weight. However, substantially unprocessed soy materials, used in the food industry, generally have objectionable food smells which the refining, bleaching and deodorizing of the cosmetic grade soy materials ameliorate by removal and they are not generally used for skin care purposes. Though soy flour and soy molasses have been described as being utilized for dermatological applications such as in U.S. Pat. Nos. 2,876,164 and 5,871,743. Such patents are typical of soy materials which have been processed and chemically modified. The soy flour described in U.S. Pat. No. 2,876,164 is described as being totally defatted and treated with organic fat solvents and stabilized with organic acids.

SUMMARY OF THE INVENTION

It is an object of the present invention to provide a relatively mild but effective skin care preparations based on different types of food grade soy flour (or soy derived materials such as oils and waxes) in amounts which provide improved effectiveness with respect to any or all of (a) skin detoxification and makeup removal, (b) exfoliation and (c) moisturization, without the harshness associated with cosmetic grade soy. The food grade soy flour is minimally processed, either physically or chemically, whereby food nutrients and nutritional characteristics are maximally maintained.

It is another object of the present invention to provide a method of skin care treatment using a sequence combination of the skin care preparations.

It is a further object of the present invention to provide the skin care preparations either separately for the individual purposes of detoxification, exfoliation and moisturization or as part of an overall skin treatment regimen or system.

It is a still further object of the present invention to provide the skin care preparations as soap bar preparations which are quickly, efficiently and effectively utilized as part of a normal cleaning, bathing or showering activity.

It is yet another object of the present invention wherein skin care preparations are provided which simultaneously provide several skin care effects, normally requiring different preparations.

It is still yet another object of the present invention to provide formulations which remove, mask or otherwise reduce or eliminate objectionable food smells of the food grade soy flour.

These and other objects, features and advantages of the present invention will become more evident from the following discussion.

Generally the present invention comprises individual skin care preparations comprised of food grade soy materials (flour, oil, wax, etc.) in a suitable carrier material. In particular the present invention comprises food grade soy flour contained in a carrier such as a soap bar base (whether of natural or non-natural (artificial) soap materials) and a method for effecting skin care utilizing the skin care preparations. The skin care comprises the effects of detoxification (with or without makeup removal), exfoliation of dead skin cells, and moisturization. Different soy flours provide skin care preparations suitable for different effects of detoxification (with or without makeup removal), exfoliation and moisturization. Soy flour, in accordance with the present invention, is defined as flour derived from soy beans to food industry standards for human and/or animal ingestion for nutritional purposes. Food grade soy flour is processed (e.g., hulling, milling and roasting) to only a limited extent for food preparation purposes with the soy flour retaining a substantial portion of its original nutrients and it is distinguished from soy flour or other products of an industry recognized cosmetic grade which have been extensively processed with refining, bleaching and deodorizing. The skin care preparations of the present invention are accordingly not cosmetic preparations but are comprised essentially of food materials added to non-cosmetic soap bases with beneficial effect as described.

Food grade soy materials, since they are originally and primarily intended for ingestion, are mild and may be present in almost any percentage composition and are limited by manufacturing requirements in the various forms. The food grade soy flour is present in a separate soap bar for each of the above effects in a weight percentage for each bar ranging from about 1% up to about 30% soy flour content by weight, with a preferred content range of about 3 to 15% and a most preferred range of about 5 to 7%. It is noted that commercial skin care preparations such as bars, cremes, lotions, and shampoos touted as containing beneficial soy, actually contain no more than 1% by weight of cosmetic grade soy content and most often only a small fraction of a percent. Some utilizations, with more than 1% soy content, such as in U.S. Pat. No. 2,876,164, require extensive chemical treatment and the use of acid stabilizers.

Soap bars containing three types of soy flour are used in the skin care system of the present invention. A first bar is formulated with soy flour to provide detoxification with the bar being utilizable to remove makeup as part of the detoxification. A second bar is formulated with soy flour to provide exfoliation and a third bar is formulated with soy flour to provide moisturization. All the soy flours are of a food grade (not a cosmetic grade or with extensive chemical modification and adjuncts) with variations in fat content effected by standard methods such as with chemical separation, roasting and expeller pressing. In addition, the soy flours are not chemically treated to render them non-ingestible prior to incorporation within the soap bar bases.

DETAILED DESCRIPTION OF THE INVENTION

Food grade soy flour is processed from various beans, with various fat contents and particle sizes with different processed soy flours having been discovered to have different skin treatment characteristics for detoxification with makeup removal, exfoliation and moisturization. In order to mask and make the characteristic objectionable food odor of food grade soy flour a strong natural fragrance such as eucalyptus and menthol essential oils are added to the soap bar. In addition, the fragrance helps provide the user with a feeling of cleanliness as well. The fragrance should be selected to be strong and also be able to blend with the soy flour odor without becoming objectionable. The fragrance(s) comprise between 0.05 and 3%, and preferably 0.4 to 1.5% of the bar. The preferred fragrance(s) is (are) preferably all natural, and in a preferred embodiment have therapeutic or aromatherapeutic properties.

In accordance with the present invention, soy flour of specific skin care characteristics is included in a commercially available or commercially known bar base, which may be natural, or non natural, chemically derived, with the natural ones being preferred.

Typical soap bars contain fats and oils that react with lye such as solid fats like coconut oil, palm oil, tallow or lard which form hard bars resistant to dissolving. Oils such as olive, soybean oil (to the extent used as described) or canola oil provide softer soaps such as Castile soap. Reaction with lye provides glycerine (an emollient or skin softener) as well as sodium reaction products of the fats and oil. Other added ingredients include polyethylene glycols such as PEG-6 methyl ether as a surfactant as well as other surfactants, detergents, emulsifiers and/or thickeners. Water softeners may be added, as well as perfumes, dyes, preservative and antibacterials. It is noted that oils undesirably impede sudsing whereas the soy flour does not. Sudsing importantly provides the user with a feeling of greater cleanliness and is preferably retained and enhanced when possible.

The following is a typical composition of a commercial soap for sensitive skin:

Sodium Cocoyl Isethionate (synthetic detergent), Stearic Acid (fatty acid), Sodium Tallowate (rendered beef fat), Water, Sodium Isethionate (synthetic detergent), Coconut Acid, Sodium Stearate (detergent), Cocamidopropyl Betaine (synthetic detergent), Sodium Cocoate (coconut oil) or Sodium Palm Kernelate (palm kernel oil), Sodium Chloride (table salt), Titanium Dioxide (cosmetic whitener), Sweet Almond Oil, Rosewood Oil (essential oil), Tetrasodium EDTA (salt; water softener), Trisodium Etidronate (preservative), BHT (preservative), Cedarwood Oil (essential oil), Rose Oil (essential oil). May also contain Disodium Cocamido Mea Sulfosuccinate (synthetic detergent), Cetyl Alcohol, and Tocopheryl Acetate (Vitamin E).

Detoxification (Makeup Removal)

Bar soaps are normally not utilized for purposes of detoxification and/or makeup removal. Instead, such functions are typically performed with the use of creams and lotions. However, in accordance with the present invention a bar soap having qualities of removal strength for drawing out toxins and loosening of dead skin cells, is used for the skin care step of detoxification and makeup removal. The base material of the bar is typically of a standardized soap bar formulation and is made in accordance with known prior art, such as described above. Soy flour is added to the bar base formulation, to provide the characteristics required for each of the skin care steps. For the requisite operative characteristics of the bar soap for purposes of detoxification and makeup removal, the added soy flour is preferably a full fat flour from a low fat (not defatted) bean of 100 mesh particle size and is generally of a standard food grade. To further facilitate the detoxification and makeup removal function, materials such as Hawaiian mud salt are added to the bar in amounts ranging from 0.5% to about 1.0% and preferably about 0.75%. The amount of soy flour in the bar preferably ranges from about 3 to 15% by weight with a most preferred range of about 5-7%. Makeup removal and general cleansing is thus effected at the same time with a single bar of soap.

Rosy 100, designation for a roasted full fat soy flour, available as a food soy product from National Products, Inc., Grinnell, Iowa, is an example of a soy flour suitable for detoxification in accordance with the present invention and is preferred especially since it does not have as much of an objectionable bad odor typical when soy flour is wetted. Since it has a higher fat and thus higher lecithin content, the soy flour provides the requisite drawing out of moisture and pollutants from skin to effect the detoxification.

An example of components of a typical soap bar base, as used with the detoxification and makeup removal soy flour has the following base formulation materials:

Sodium palmate, sodium cocoate, water, glycerin, butyrospermum parkii (shea butter), theobroma cacao (cocoa) seed butter, sodium bicarbonate, pentasodium pentetate, and iron oxide. Hawaiian mud salt is added to these base materials as well as the soy flours described and the masking fragrance materials.

Exfoliating

The soy flour utilized for the exfoliation bar is preferably a partially defatted low fat soy flour with soy flour of coarser grit to controllably enhance abrasiveness. The bean is partially roasted to defat it. A full roast is to be avoided since the flour made from such process results in a material which is hard and difficult to dissolve during use. Because of the partial roasting of the HILO flour it is more soluble upon soaping up.

Examples of suitable flours, also available from National Products, Inc., are low fat flours designated as HILO (Hi-PDI Low Fat) such as HILO 100, which is preferred. As with the detoxification bar, the total soy flour content ranges from 1-15% and is preferably between 5-7% by weight. Furthermore the soy flour in the bar is preferably about 60% Rosy 16 because of its coarser grit (compared to the Rosy 100) suitable for exfoliation and about 40% of the HILO partially defatted or low fat soy flour to soften the abrasiveness (thus making it suitable for every day use without excessive exfoliation-with raw skin) and to rebuild collagen to at least partially compensate for the loss of collagen and dead skin cells. The exfoliating bar is otherwise preferably made with the base materials including collagen, as used in commercially available exfoliating bar soaps. The above formulation for the base material of the detoxification bar is similarly utilized as base materials for the exfoliating bar and the moisturizing bars as well. The specific exfoliating soy flours, as described are added to the soap base materials. The same fragrance additives, as used with the detoxifying bar, are added as well.

Moisturizing

Moisturizing soap bars contain a plethora of materials including olive oil, shea and cocoa butter, etc. The moisturizing bar of the present invention, in addition to the typical emollients contains a fully defatted soy flour of a finely ground 100 mesh. The flour is usually prepared with the oil being separated from the flour by being expressed in a powder expeller or cold pressed. The soy flour-containing moisturizing bars of the present invention have a lecithin content of less than 1% and is effective in smoothing out new skin brought to the surface by the exfoliating bar. HILO 600 is ideal for adding moisture to skin rather than drawing it out as a result of its low lecithin content. The soy flour for the moisturizing skin treatment bars is preferably a high (¼% by weight of the soy flour) lecithin containing organic soy flour such 1% JADE 1000 (available from Soylink and described in U.S. Pat. No. 7,097,871). The lecithin content serves as a moisturizer in small quantities (lecithin draws moisture from skin when used in larger quantities) and the Jade 1000 is also generally used as a skin lightener. The specific moisturizing soy flours, as described, are added to the soap base materials. The same fragrance additives, as used with the detoxifying bar, are added as well.

Skin Care Regimen

The three bars of the present invention may be used separately for the stated purposes or they can be used in seriatim in a skin care regimen starting with detoxification, then exfoliation and ending with moisturization. It is preferred that the exfoliation follow shortly after the detoxification to take advantage of the loosening effect of dead skin cells of the detoxification soap bar. Moisturization can be provided by the third bar type at any desired time. It is however preferred that the moisturization bar be used directly after the exfoliation in order to take advantage of the smoothing effect of the moisturizing bar of the present invention which smoothes out any rough skin caused by the exfoliation. Thus, it is preferred that all three bars be used in a single shower session to effect the normal cleansing of the shower and the skin care effects described above without the necessity of separate procedures and time and with maximum skin care effect.

Manufacture of the Respective Soap Bars

Typical bars of the present invention are formulated in standard 4.5 ounce sizes and, when used on a daily basis, are effectively used for about thirty days. The base material such as the soap bar ingredients are liquefied such as by heating and the soy flour is mixed into the base material to form a homogeneous mixture. The finished skin preparation material is then prepared accordingly to art recognized methods. For bar soaps, the liquefied composition is poured into molds, is hardened, cut, pressed, and stamped in accordance with the type of soap manufacturing procedure and machinery being used.

It is understood that the above specific examples of soy flours, carrier and bar compositions and the like are merely exemplary of the present invention and that changes in compositions, composition preparations, relative quantities and the like may vary in accordance with the following claims

What is claimed is:

1. A skin care preparation comprising a skin care preparation base with a substantial weight percentage thereof of a food grade soy material, wherein the food grade soy material is formulated to provide at least one of characteristics of skin detoxification and makeup removal, exfoliation, and skin moisturization, wherein for skin detoxification and makeup removal the food grade soy material is formulated from a full fat flour derived from low fat soy beans, wherein for exfoliation the food grade soy is formulated from a partially roasted defatted flour with a coarse grit, and wherein for skin moisturization the food grade soy is formulated as being finely ground and defatted.

2. The skin care preparation of claim 1, wherein the food grade soy material comprises at least one of a soy oil, soy wax and soy flour.

3. The skin care preparation of claim 2, wherein the food grade soy material comprises from 1 to 30% by weight of the total skin care preparation.

4. The skin care preparation of claim 2, wherein the food grade soy material comprises a soy flour.

5. The skin care preparation of claim 4, wherein the skin care preparation base is a soap bar.

6. The skin care preparation of claim 5, wherein the food grade soy material comprises from 3 to 15% by weight of the soap bar.

7. The skin care preparation of claim 1 wherein the food grade soy flour is a full fat flour derived from low fat soy beans with a particle size and grit suitable for loosening dead skin cells.

8. The skin care preparation of claim 1, wherein the skin care preparation further contains Hawaiian mud salt.

9. The skin care preparation of claim 1, wherein the skin care preparation comprises a mixture of partially roasted defatted food grade soy flour and a full fat food grade soy flour.

10. The skin care preparation of claim 1, wherein the food grade soy flour includes an organic soy flour with a lecithin content of up to ¼% by weight of the soy flour.

11. The skin care preparation of claim 1, wherein the food grade soy material has an odor and wherein the skin care preparation further comprises a fragrance of sufficient strength and quantity to mask the odor.

12. The skin care preparation of claim 11, wherein the fragrances is comprised of at least one eucalyptus and menthol essential oils.

13. The skin care preparation of claim 5, wherein the soap bar contains no soy oils in quantities which reduce sudsing.

14. A method of skin care comprising the steps of: a) detoxifying the skin with the soap bar of claim 5, b) exfoliating dead skin cells loosened by the soap bar by cleansing the skin with a second soap bar comprising food grade soy flour comprised of a partially roasted defatted flour with a coarse grit suitable for exfoliation; and c) moisturizing the skin with a third soap bar comprising a finely ground and defatted food grade soy flour and lecithin in amounts of up to ¼% by weight of the soy flour.

15. The method of skin care of claim 14, wherein the steps of detoxifying the skin, exfoliating dead skin cells and moisturizing the skin are carried out in a single shower session with the skin being smoothed by the third soap bar from any rough effects engendered by the first and second soap bars.

16. The skin care preparation of claim 3, wherein the skin care preparation base is a soap bar.

* * * * *